US006433011B1

(12) United States Patent
Chung et al.

(10) Patent No.: US 6,433,011 B1
(45) Date of Patent: Aug. 13, 2002

(54) METHOD FOR INHIBITING FORMATION OF ABERRANT CRYPT FOCI IN THE COLON OF A MAMMAL

(75) Inventors: Fung-Lung Chung, Yorktown Hts.; Bandaru Reddy, Suffern; C. Clifford Conaway, Mahopac, all of NY (US)

(73) Assignee: American Health Foundation, Valhalla, NY (US)

( * ) Notice: Subject to any disclaimer, the term of this patent is extended or adjusted under 35 U.S.C. 154(b) by 0 days.

(21) Appl. No.: 09/520,513

(22) Filed: Mar. 8, 2000

(51) Int. Cl.$^7$ .................. A61K 31/21; A61K 31/26
(52) U.S. Cl. ...................... 514/514; 514/741
(58) Field of Search ................ 514/514, 741

(56) References Cited

U.S. PATENT DOCUMENTS

RE36,784 E 7/2000 Cho et al. ............... 424/94.1

OTHER PUBLICATIONS

O.S. Sohn et al, "Enhancement of Rat Liver Microsomal Metabolism of Azoxymethane to Methylaxoymethanol . . . N–Nitrosodimethylamine" *Cancer Research* vol. 47 (1987) pp. 3123–3129.
S. Sugie et al., "Inhibitory Effects of Benzyl Thiocyanate and Benzyl Isothiocyanate on Methylazoxymethanol . . . Carcinogenesis in Rats" *Carcinogenesis* vol. 15, No. 8 (1994) pp. 1555–1560.
M.J. Iatropoulos et al., "Three Month Toxicity Study of Phenethyl Isothiocyanate in Fischer 344 Rats" American Health Foundation, *AHF Study* No. R–1508, Final Report (1995), pp. 1–182.
Lin, H.J.,, et al (1998)Glutathione transferase null genotype, broccoli, and lower prevalence of colorectal adenomas, Cancer Epidemiol., Biomark.. Prev. 7, 647–652.
Ketterer, B., et al (1998) Dietary isothiocyanates as confounding factors in the molecular epidemiology of color cancer. Cancer Epidemiol., Biomark.. Prev. 7, 647–652.
Zhang, V, et al (1994) Anticarcinogenic activities of organic isothiocyanates: chemistry and mechanisms. Cancer Res. 54 (Suppl.), 1976s–1986s.
Chung, F.L. et al (1992) New potential chemopreventive agents for lung carcinogenesis of tobacco–specific nitrosamine. Cancer Res. 52, 2719s–2722.
McLellan, E.A. et al (1988) Aberrrant crypts: potential preneoplastic lesions, in the murine colon Cancer Res. 51: 5270–5274.
Pretlow, T.P. et al (1992) Aberrant crypts in human colonic mucosa: putative *Preneoplastic lesions*. J. Cell Biochem 166 (suppl.) 55–52.
Wargovich, M.J. et al (1996) Aberrant crypts as a biomarker for colon cancer: evaluation of potential chemopreventive agents in the rat. Cancer Epidemiology, Biomarkers and Prev. 5:355–360.

Jiao, D. et al (1997) Chemopreventive activity of thiol conjugates of isothiocyantes for lung tumorigenesis. Carcinogenesis 18: 2143–2147.
Chung, F.L. et al (1997) Chemopreventive potential of thiol conjugates of isothiocyanates for lung tumorigenesis. J. Cell Biochem (suppl.) 27: 76–85.
Kassahun, K., et al (1997) Biotransformation of the naturally occurring isothiocyanate sulforaphane in the rat: identification of phase 1 metabolites and glutathione conjugates. Chem. Res. Toxicol. 10: 1228–1233.
Jiao, D., et al (1996) Inhibition of N–nitrosodimethylamine demethylase in rat and human liver microsomes by isothiocyanates and their glutathione, L–cysteine, and N–acetyl–L–cysteine conjugates. Chem. Res. Toxicol., vol. 9 (6) : 932–938.
Conway, C.C et al (1996) Inhibition of rat liver cytochrome P450 Isozymes by isothiocyanates and their conjugates: A structure–activity relationship study. Carcinogenesis, 17: 2423–2427.
Chung, F.L., et al. Chemoprevention of lung carcinogenesis by aromatic isothiocyanates. In: Cancer chemoprevention, CRC Press Inc. pp227–245, 1992.
Sugie, S. et al (1994) Inhibitory effects of benzyl thiocyanate and benzyl isothiocyanate on methylazoxymethanol acetate–induced intestina carcinogenesis in rats. Carcinogenesis 15: 1555–1560.
Wattenberg, L.W. "Inhibition of Carcinogenic Effects of Polycyclic Hydrocarbons by Benzyl Isothiocyanate and Related Compounds" J. Natl. Cancer Inst., 58, (1977) pp 395–398.
Stoner, G.D., et al. "Inhibitory Effects of Phenethyl Isothiocyanate on N–Nitrosobenzylmethylamine Carcinogenesis . . . " Cancer Res., 51, (1991) pp 2063–2068.
McLellan, E.A., et al. "Sequential Analyses of the Growth and Morphological Characteristics of Aberrant Crypt Foci: Putative Preneoplastic . . . " Cancer Res., 51, (1991) pp 5270–5274.
Reddy, B.S., et al. "Evaluation of Cyclooxygenase–2 Inhibitor for Potential Chemopreventive Properties in Colon Carcinogenesis." Cancer Res., 56, (1996) pp 4566–4569.
Zheng, G.–Q., et al. "Phenylalkyl Isothiocyanate–Cysteine Conjugates as Glutathione S–Transferase Stimulating Agents." J. Medicinal Chem., 35, (1992) pp 185–188.
Gerhäuser, C., et al. "Cancer Chemopreventive Potential of Sulforamate, a Novel Analogue of Sulforaphane That Induces Phase 2 . . . " Cancer Res., 57, (1997) pp 272–278.

(List continued on next page.)

*Primary Examiner*—Dwayne C. Jones
*Assistant Examiner*—C. Delacroix-Muirheid
(74) *Attorney, Agent, or Firm*—Ladas & Parry

(57) ABSTRACT

A method is provided for inhibiting the development of colon tumorigenesis in a mammal by administering to the mammal a pharmacologically effective amount of an isothiocyanate selected from the group consisting of sulforaphane and phenethyl isothiocyanate.

12 Claims, 2 Drawing Sheets

OTHER PUBLICATIONS

Chen, Y.-R., et al. "Molecular Mechanisms of c–Jun N–terminal Kinase–mediated Apoptosis Induced by Anticarcinogenic Isothiocyanates." J. Biol. Chem., 273, (1998) pp 1769–1775.

Huang, C., et al. "Essential Role of p53 in Phenethyl Isothiocyanate–induced Apoptosis." Cancer Res., 58, (1998) pp 4102–4106.

Yu, R., et al. "Chemopreventive Isothiocyanates Induce Apoptosis and Capase–3–like Protease Activity." Cancer Res., 58, (1998) pp 402–408.

Sekharam, M., et al. "Suppression of Fibroblast Cell Cycle Progression in G1 Phase by N–Acetylcysteine" Toxicol. And Appl. Pharm., 149, (1998) pp 210–216.

Chung, F.–L., et al. "New Potential Chemopreventive Agents for Lung Carcinogenesis of Tobacco–specific Nitrosamine." Cancer Res., 52, (1992) pp 2719s–2722ss.

Wilkinson, J.T., et al. "Effect of alkyl chain length on inhibition of N–nitrosomethylbenzylamine–induced . . . " Carcinogenesis, 16, (1995) pp 1011–1015.

Rao, C.V., et al. "Enhancement of Experimental Colon Carcinogenesis by Dietary 6–Phenylhexyl Isothiocyanate." Cancer Res., 55, (1995) pp 1–8.

Stoner, G.D., et al. "Enhancement of esophageal carcinogenesis in male F344 rats by dietary phenylhexyl isothiocyanate." Carcinogenesis, 16, (1995) pp 2473–2476.

Steinmetz K.A., et al. "Vegetables, fruit, and cancer, I. Epidemiology," Cancer Causes and Control, 2, (1991) pp 325–357.

Chung, F.–L. "Chemoprevention of Lung Carcinogenesis by Aromatic Isothiocyanates." In: Cancer Chemoprevention, Edition, (Wattenberg, L., et al.)CRC Press (1992) pp 227–245.

Hecht, S.S. "Chemoprevention by Isothiocyanates." J. Cell. Biochem., Suppl., 22, (1995) 195–209.

Levine, B.S. "Thirteen Week Oral Toxicity Study of Phenethyl . . . " NCI Contract No. NO1–CN–25508–01. Toxicol. Res. Lab., University of Illinois at Chicago(1995) pp 1and 7–16.

METHOD FOR INHIBITING FORMATION OF ABERRANT CRYPT FOCI IN THE COLON OF A MAMMAL

FIELD OF INVENTION

This invention relates to treatment for the inhibition or reduction of colon tumorigenesis in a mammal by the administration of a pharmaceutical compound.

BACKGROUND OF INVENTION

Evidence from epidemiological studies suggests an association of consumption of cruciferous vegetables and a reduced risk of colon cancer (31). Although a number of compounds in these vegetables may collectively cause the beneficial effects, there has been a need to identify the exact role of each compound that contributes to the protective effects. Ample data from laboratory animal studies have shown that isothiocyanates (ITCs), one of the major constituents of cruciferous vegetables, are promising chemopreventive agents against cancers at various sites, including lung, esophagus, liver, mammary, and bladder (3, 32, 33). These laboratory results support a potential role of dietary ITCs in reducing risk of certain human cancers. However, it is well known to those of skill in the art that chemopreventive agents affect different tissues differently.

Previously, for example, it has been reported that while phenylhexyl ITC, a synthetic homologue of PEITC, is a potent inhibitor of lung tumorigenesis, it enhanced colon and esophagus tumorigenesis in rats, possibly due to its tissue cytotoxicity at the dose level studied (29, 30). These results illustrate the importance of considering tissue specificity and of choosing the appropriate dose range for specific tissues in chemoprevention studies.

A recent case-control study reported that broccoli consumption is linked to a lowered risk of colon cancer, and the protective effect is especially evident in individuals with a glutathione transferase (GST) M1 null genotype (1). Because GSTs facilitate the conjugation of ITCs resulting in their excretion as the N-acetylcysteine NAC) conjugates via the mercapturic acid pathway, it has been suggested that the ITC compounds in broccoli may play a role in the protection of human colon cancer (2). Sulforaphane (SFN) is the predominant ITC found in broccoli which has been studied for its chemopreventive potential due to its activity in the induction of phase II enzymes involved in carcinogen detoxification and elimination (3). However, so far no animal data is available regarding the effects of SFN on colon tumorigenesis. Several laboratory animal studies have shown that phenethyl ITC (PEITC), a principal constituent in watercress, is a potent chemopreventive agent for cancers of the breast, lung, and esophagus (4, 5, 6). However, there is insufficient data for PEITC on colon cancer.

Considering the natural abundance of SFN and PEITC in broccoli and watercress, respectively, and their potential as chemopreventive agents, it is surprising that little is known about the effects of these agents on colon tumorigenesis. A lower homologue of PEITC, benzyl ITC (BITC) has been shown to inhibit colon tumor incidence in AOM treated rats during the initiation phase, but not during the post-initiation phase (34). Another short-term study, however, has reported that both PEITC and BITC given in the diet at similar dose levels were inactive towards ACF formation, in fact, BITC was found to slightly induce ACF formation (10). By contrast, the present inventors have now demonstrated for the first time that both PEITC and SFN inhibit colonic ACF, independent of whether they are administered before or after carcinogen exposure.

SUMMARY OF THE INVENTION

There is provided in accordance with one embodiment of the invention a method for inhibiting tumor development in a mammal. The method comprises administering to the mammal a pharmacologically effective amount of an isothiocyanate selected from the group consisting of sulforaphane and phenethyl isothiocyanate. The sulforaphane may be isolated from broccoli and the phenethyl isothiocyanate may be isolated from watercress. The isothiocyanate is preferably administered to the mammal as a purified compound, either alone or in a composition with a pharmacologically acceptable carrier, excipient or diluent or with a beverage or foodstuff.

In a preferred embodiment of the invention, the mammal is a human and the isothiocyanate is administered to the human as a dietary supplement. In a preferred treatment regimen, the isothiocyanate is administered to the human in a dosage of between about 0.5 and 12 mg/kg body weight per day.

In another embodiment of the invention there is provided a method for treating colon tumor formation in a mammal in need of such treatment. The method comprises administering to the mammal a pharmacologically effective amount of an isothiocyanate selected from the group consisting of sulforaphane and phenethyl isothiocyanate.

The above and other features and advantages of the invention will be found in the detailed description which follows below.

DETAILED DESCRIPTION

Figure 1:
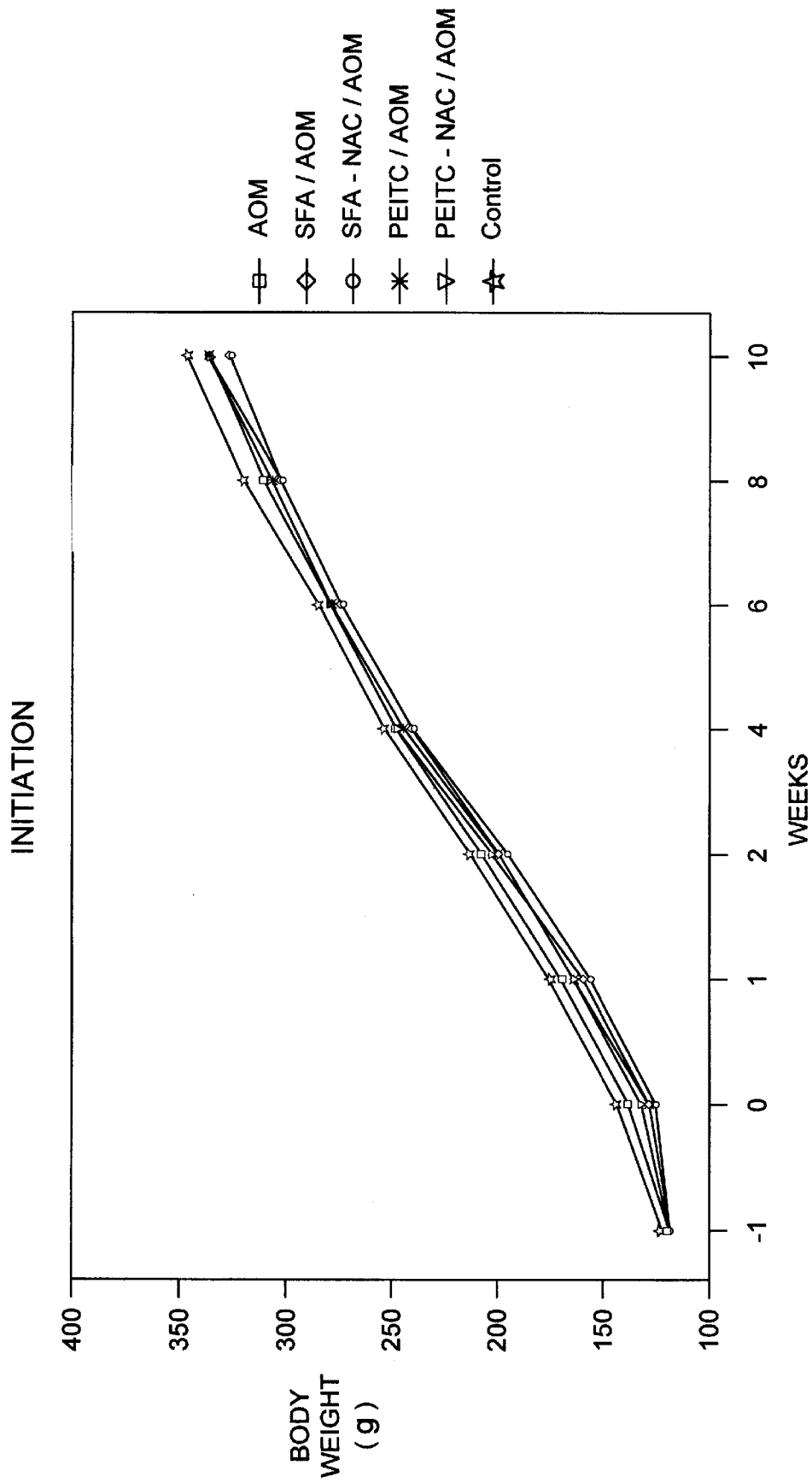
FIG. 1 is a graph showing the body weight over time of rats treated with isothiocyanates in accordance with the invention before (initiation) AOM treatment and rats in a control group.

As used herein, the abbreviations have the following meanings: ITCs, isothiocyanates; SFN, sulforaphane; PEITC, phenethyl isothiocyanate; BITC, benzyl isothiocyanate; AFC, aberrant crypt foci; NAC, N-acetylcysteine; AOM, azoxymethane; NNK, -(4-methylnitrosamino)-1-(3-pyridyl)-2-butanone; CYP, cytochrome P450; NDMA, N,N-dimethylnitrosamine. All references cited herein are hereby specifically incorporated into this disclosure by reference.

The inventors designed a bioassay to examine whether SFN and PEITC can inhibit the formation of aberrant crypt foci (ACF) induced by azoxymethane (AOM) in Fischer rats. ACF has been recognized as an early preneoplastic lesion of colon cancer (7–9) and it is generally observed that agents that inhibit colonic ACF formation would show chemopreventive activity against colon cancer (10). The inventors also included in this study the NAC conjugates of SFN and PEITC since their previous studies showed that certain ITC-NAC conjugates are promising chemopreventive agents for lung tumorigenesis, probably by a gradual release of the parent ITCs via a dissociation reaction (11, 12). The structures of SFN and PEITC and their NAC conjugates are shown below. Two treatment regimens in which SFN and PEITC or their NAC conjugates were administered either after (post-initiation) or before (initiation) AOM treatment were used in the bioassay in order better to define the possible mechanism of action.

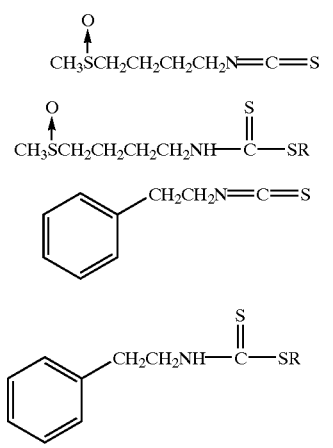

Male F344 rats were from Charles River (Kingston, N.Y.). They were fed AIN-76A diet (5% corn oil) and tap water ad libitum. Animals were maintained under standard conditions (12-h light/12-h dark cycle, 50% relative humidity at 21° C.). At six-weeks of age, they were randomly divided into six per groups as shown in Table 1, except for the control groups 10 to 14, which consist of three animals. PEITC and SFN were purchased from Aldrich Chemical Company (Milwaukee, Wis.) and LTK Labs, Inc. (St. Paul, Minn.), with purity >99% and >97%, respectively. The corresponding NAC conjugates were prepared by a published method (13, 26). The purity of the conjugates was greater than 97% as determined by high-performance liquid chromatography. AOM obtained from Ash-Stevens (Detroit, Mich.) was dissolved in saline and administered subcutaneously once a week for two weeks. SFN and PEITC in corn oil and the NAC conjugates in saline (10% DMSO) were given by gavage. Groups 2 to 5 were given 5 $\mu$mol SFN or PEITC or 20 $\mu$mol of the NAC conjugates, three doses each week for eight weeks, beginning two days after the last dose of AOM. Groups 6 to 9 were treated with three doses of ITC compounds (20 $\mu$mol ITC or 50 $\mu$mol ITC-NAC) once daily and the last dose was given 2 hr before AOM dosing. This dosing regimen was repeated during the second week of AOM dosing. Groups 10 to 13 were treated with ITCs (5 $\mu$mol/dose) or the conjugates (20 $\mu$mol/dose) only, three times weekly for eight weeks. Group 14 served as the control group. The bioassay was terminated at week 10 after the second AOM treatment. The colon was processed for microscopic examination and the ACF were recorded using a standard procedure described previously (14). ACF were distinguished from the surrounding normal crypts by their increased size, significantly increased distance from lamina to basal surface of cells, and the easily discernable pericryptal zone. For statistical analysis, means were compared among the groups using one-way analysis of variance (ANOVA) followed by Fisher's protected t-test.

Figure 2:
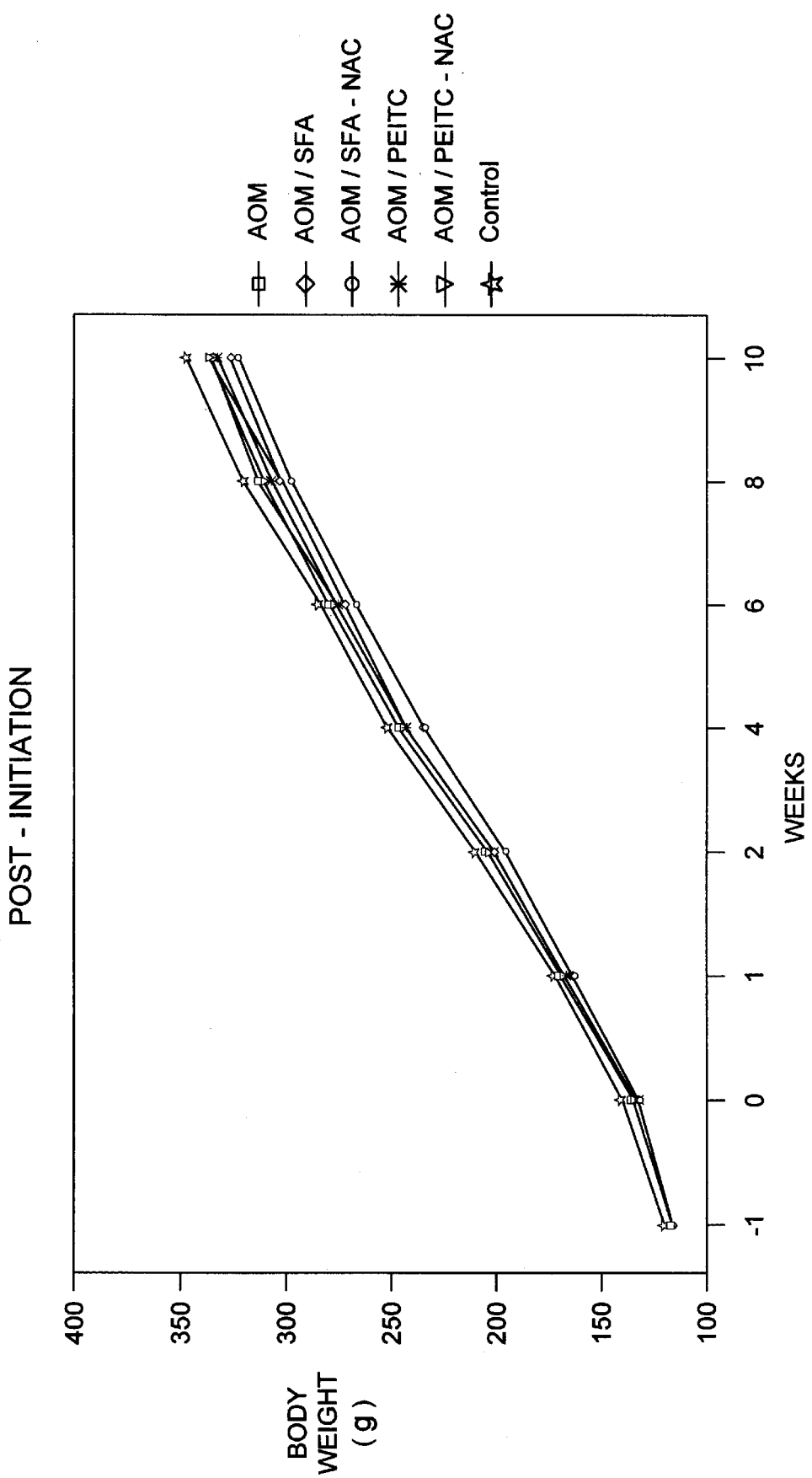
FIG. 2 is a graph showing the body weight over time of rats treated with isothiocyanates in accordance with the invention after (post-initiation) AOM treatment and rats in control group.

No significant differences in body weights were seen in any of the treated groups compared with the control group, indicating that doses of ITCs and the conjugates used did not cause overt toxicity (see FIGS. 1 and 2). This bioassay showed that post-treatment by oral administration of SFN and PEITC at 5 $\mu$mol three doses weekly for eight weeks and their NAC conjugates at 20 $\mu$mol by the same regimen inhibited the formation of ACF. These treatments reduced the total ACF from 153 to 100–116 (p<0.01) and multicrypt foci (>4 crypts/focus) from 52 to 27–37 (p<0.04) as shown in Table 1 (Groups 1 to 5). Since the ITC conjugates are presumably less toxic than the parent ITCs, the doses of the conjugates were 4 times that of SFN and PEITC (15, 16). However, the inventors did not find significant difference in the inhibition of ACF between the ITCs and their NAC conjugates, suggesting the conjugates themselves are not as active. Similar dose-effect relationships were observed previously between parent ITCs and their conjugates towards the inhibition of lung tumorigenesis (7). These results, together with those from the inventors' earlier studies (17, 18), suggest that ITC conjugates render their inhibitory activity in part by the deconjugation to the parent ITCs. Although the mechanism of inhibition of ACF at the post-initiation phase is not currently clear, recent studies have shown that PEITC and related ITCs induce p53-dependent or c-jun kinase-mediated apoptosis in cultured cells (19–21). In addition, NAC produced by deconjugation is a known antioxidant which has been recently shown to inhibit mouse fibroblast cell proliferation by blocking cell in G1 phase (22). All these activities could have contributed to the inhibition of ACF formation during the post-initiation of ACF formation.

Studies by the inventors and others showed that pretreatment of animals with PEITC and other related ITCs blocked chemical-induced tumorigenicity by inhibiting cytochrome p450 (CYP) enzymes responsible for the activation of carcinogens, and consequently reducing DNA damage (23–25). The inventors investigated the effects of pretreatment with SFN and PEITC on the AOM-induced colonic ACF formation in Fischer rats. The results showed that pretreatment with SFN or PEITC significantly decreased total number of ACF from 153 to 109 (p<0.004) or 115 (p<0.01), respectively, and multicrypt foci (>4 crypts) from 52 to 35 (p<0.03) for both compounds (Table 1 below). The inventors have previously shown that PEITC and PEITC-NAC are inhibitors of N,N-dimethylnitrosamine (NDMA) demethylase (CYP2E1) in rat liver microsomes (26). Like NDMA, AOM is metabolically activated by CYP2E1 to methyazoxymethanol which can yield a DNA methylating species (27). Thus, inhibition of CYP2E1 by these agents in the rat liver may constitute an important mechanism for the inhibition, since CYP enzyme activity in colonic tissue is low compared to that in liver (24). SFN-NAC also reduced total AFC to 120 (p<0.02), however, it had no significant effect on multicrypt foci (>4 crypts/focus, 15% inhibition). PEITC-NAC, on the other hand, appeared to enhance ACF formation (total number of ACF is 198, p<0.002; number of multicrypt foci is 74, p<0.008) (Table 1). The adverse effect caused by PEITC-NAC is unexpected in view of the inhibition by its parent ITC. At present, it is not clear as to why there is such a sharp contrast towards ACF formation for PEITC-NAC compared to other ITC compounds studied here.

TABLE 1

Effects of SFN and PEITC on the formation of aberrant crypt foci induced by AOM

| Treatment Group[a] | Dose of ITC Compounds ($\mu$mol) | Average Body Weight at Termination | Number of aberrant crypt foci >4 Crypts | Total |
|---|---|---|---|---|
| 1. AOM | — | 310 | 52 | 153 |
| 2. AOM→SFN | 5 | 301 | 30 (42)[b,c] | 103 (33)[d] |
| 3. AOM→SFN-NAC | 20 | 297 | 31 (40)[c] | 116 (24)[c] |
| 4. AOM→PEITC | 5 | 306 | 27 (48)[c] | 100 (35)[d] |
| 5. AOM→PEITC-NAC | 20 | 313 | 38 (27)[f] | 113 (26)[e] |
| 6. SFN→AOM | 20 | 310 | 35 (33)[f] | 109 (29)[c] |
| 7. SFN-NAC→AOM | 50 | 304 | 44 (15) | 120 (22)[c] |
| 8. PEITC→AOM | 20 | 307 | 35 (33)[f] | 115 (25)[c] |
| 9. PEITC-NAC→AOM | 50 | 303 | 74 (−42)[c] | 198 (−29)[e] |
| 10. SFN | 5 | 309 | 0 | 0 |
| 11. SFN-NAC | 20 | 312 | 0 | 0 |
| 12. PEITC | 5 | 333 | 0 | 0 |
| 13. PEITC-NAC | 20 | 301 | 0 | 0 |
| 14. Control | — | 320 | 0 | 0 |

[a]In Groups 2 to 5, ITC compounds are administered during post-initiation phase and in Groups 6 to 9 ITC compounds were given during initiation phase.
[b]Percent of inhibition compared to Group 1.
[c]Significantly different from Group 1 at $p < 0.01$.
[d]Significantly different from Group 1 at $p < 0.0001$
[e]Significantly different from Group 1 at $p < 0.001$
[f]Significantly different from Group 1 at $p < 0.05$

Preferred Dose Levels and Toxicity Considerations

In the above study a colon carcinogen, AOM, was used to initiate precancerous lesions in the colon; the dose was considerably higher than the anticipated dose of any carcinogen to which humans would be inadvertently subjected. The chemopreventive agents were administered in two types of treatments. In the first type of treatment, rats were dosed after AOM was given with 5 $\mu$mole of either sulforaphane (SFN) [6.3 mg/kg] or phenethyl isothiocyanate (PEITC) [5.8 mg/kg] or 20 $\mu$mole of either the N-acetylcysteine conjugate of SFA (SFN-NAC) [48.6 mg/kg] or the N-acetylcysteine conjugate of PEITC (PEITC-NAC) [46.6 mg/kg] three times per week for eight weeks. In the second treatment regimen, the rats received 20 $\mu$mole of the respective ITCs or 50 $\mu$mole of the N-acetylcysteine conjugates four days per week for two weeks prior to AOM administration once each week. Symptoms of gastrointestinal toxicity or irritation (bloody mucus in feces) were observed very early in the second treatment regimen, suggesting that the dose levels used may have been in excess of a dose safe for human consumption.

Additional toxicity information regarding PEITC is available from a 90 day study in rats, in which 500, 1500, and 2500 ppm was administered in the diet (35). Dietary PEITC reduced weight gain in male rats at the high dose level by approximately 9.5% (not significant). In addition, liver weights of male rats ingesting 1500 and 2500 ppm PEITC were significantly elevated. Changes in the epithelial lining of the forestomach of both male and female rats at 2500 ppm were also observed. In another study with Beagle dogs, PEITC was administered daily in gelatin capsules. Diarrhea and vomiting, with gastrointestinal irritation, occurred sporadically at dose levels of 2 mg/kg and higher. Signs of irritation of the mucosa of the urinary bladder were reported at 4 mg/kg/day and higher. Dose related weight loss occurred in both male and female dogs, which became statistically significant in females at 8 mg/kg. No other signs or symptoms of toxicity were reported (36).

In a preliminary study in humans presently being conducted to determine the efficacy of PEITC as a chemopreventive agent for lung cancer in smokers, volunteers have been given 40 mg PEITC (approx. 0.6 mg/kg) in gelatin capsules. No adverse effects from this dose have been observed after repeated dosing every four hours.

On the basis of existing toxicity information and efficacy data, the inventors suggest the following safe dose ranges for human consumption:

| | |
|---|---|
| PEITC | 0.6 to 1.2 mg/kg body weight |
| PEITC-NAC | 6.0 to 12 mg/kg body weight |
| SFN | 0.55 to 1.1 mg/kg body weight |
| SFN-NAC | 5.5 to 11 mg/kg body weight |

The components of the present invention may be administered as a dietary supplement. For example, they may be administered orally, either alone or with water or another beverage or with a foodstuff.

There may be many modifications and variations of the methods and compounds set forth hereinabove. These modifications and variations will not depart from the scope of the invention, if defined by the following claims and equivalents thereof.

REFERENCES

1. Lin, H. J., Probst-Hensch, N. M., Louie, A. D., Kau, I. H., Witte, J. S., Ingles, S. A., Franki, H. D., Lee, E. R., Haile, R. W. (1998) Glutathione transferase null genotype, broccoli, and lower prevalence of colorectal adenomas. Cancer Epidemiol., Biomark. Prev., 7, 647–652.
2. Ketterer, B. (1998): Dietary isothiocyanates as confounding factors in the molecular epidemiology of colon cancer. Commentary re: H. J. Lin et al., Glutathione transferase null genotype, broccoli, and lower prevalence of colorectal adenomas. Cancer Epidemiol. Biomark. Prev., 7: 647–652, 1998.
3. Zhang, Y., Talalay, P. (1994) Anticarcinogenic activities of organic isothiocyanates: chemistry and mechanisms. Cancer Res., 54 (Suppl.), 1976s–1986s.

4. Wattenberg, L. W. Inhibition of carcinogenic effects of polycyclic hydrocarbons by benzyl isothiocyanate and related compounds. (1977) J. Natl. Cancer Inst., 58, 396–398.
5. Chung, F.-L., Morse, M. A., Eklind, K. I. (1992) New potential chemopreventive agents for lung carcinogenesis of tobacco-specific nitrosamine. Cancer Res., 52, 2719s–2722s, 1992.
6. Stoner, G. D., Morrissey, D. T., Heur, Y.-H., Daniel, E. M., Galati, A. J., Wagner, S. A. (1991) Inhibitory effects of phenethyl isothiocyanate on N-nitrosobenzyl-methylamine carcinogenesis in the rat esophagus. Cancer Res., 51, 2063–2068.
7. Mclellan, E. A., and Bird, R. P. (1988) Aberrant crypts: potential preneoplastic lesions in the murine colon. Cancer Res. 48, 6187–6192.
8. Mclellan, E., Medline, A., and Bird, R. P. (1991) Sequential analyses of the growth and morphological characteristics of aberrant crypt foci-putative preneoplastic lesions. Cancer Res. 51: 5270–5274.
9. Pretlow, T. P., O'Riordan, M. A., Pretlow, T. G., and Stellato, T. A. (1992) Aberrant crypts in human colonic mucosa: putative preneoplastic lesions. J. Cell Biochem. 166 (suppl.) 55–62.
10. Wargovich, M. J., Chen, C.-D., Jimenez, A., Steele, V. E., Velasco, M., Stephens, L. C., Price, R., Gray, K., and Kelloff, G. J. (1996) Aberrant crypts as a biomarker for colon cancer: evaluation of potential chemopreventive agents in the rat. Cancer Epidemiology, Biomarkers and Prev. 5: 355–360.
11. Jiao, D., Smith, T. J., Yang, C. S., Pittman, B., Desai, D., Amin, S., Chung, F.-L. Chemopreventive activity of thiol conjugates of isothiocyanates for lung tumorigenesis. Carcinogenesis, 18, 2143–2147, 1997.
12. Chung, F.-L., Jiao, D., Conaway, C. C., Smith, T. J., Yang, C. S., Yu, M. C. (1997) Chemopreventive potential of thiol conjugates of isothiocyanates for lung cancer and a urinary biomarker of dietary isothiocyanates. J. Cell. Biochem., (Suppl.) 27: 76–85, 1997.
13. Kassahun, K., Davis, M., Hu, P., Martin, B., Baillie, T. (1997) Biotransformation of the naturally occurring isothiocyanate sulforaphane in the rat: identification of phase 1 metabolites and glutathione conjugates. Chem. Res. Toxicol., 10, 1228–1233.
14. Reddy, B. S., Rao, C. V., and Seibert, K (1996) Evaluation of cycloxygenase-2 inhibitor for potential chemopreventive properties in colon carcinogenesis. Cancer Res. 56, 4566–4569.
15. Zheng, G.-Q., Kenney, P. M., Lam, L. K. T. (1992) Pheylalkyl isothiocyanate-cysteine conjugates as glutathione S-transferase stimulating agents. J. Medicinal Chem., 35, 185–188.
16. Gerhauser, C., You, M., Liu, J., Moriarty, R. M., Hawthorne, M., Mehta, R. G., Moon, R. C., Pezzuto, J. M. (1997) Cancer chemopreventive potential of sulforanate, a novel analogue of sulforaphane that induces phase 2 drug-metabolizing enzymes. Cancer Res, 57, 272–278.
17. Jiao, D., Conaway, C. C., Wang, M.-H., Yang, C. S., Koehl, W., Chung, F.-L. (1996) Inhibition of N-nitrosodimethylamine demethylase in rat and human liver microsomes by isothiocyanates and their glutathione, L-cysteine, and N-acetyl-L-cysteine conjugates. Chem. Res. Toxicol., 9, 932–938.
18. Conaway, C. C., Jiao, D., Chung, F.-L. (1996) Inhibition of rat liver cytochrome P450 isozymes by isothiocyanates and their conjugates: A structute-activity relationship study. Carcinogenesis, 16, 2423–2427.
19. Chen, Y.-R., Wang, W., Kong, A.-N. T., Tan, T.-H. (1998) Molecular mechanisms of c-jun N-terminal kinase-mediated apoptosis induced by anticarcinogenic isothiocyanates. J. Biol. Chem., 273: 1769–1775.
20. Huang, C., Ma, W.-Y., Li, J., Hecht, S. S., Dong, Z. (1998) Essential role of p53 in phenethyl isothiocyanate-induced apoptosis. Cancer Res. 58, 4102–4106.
21. Yu, R., Mandlekar, S., Harvey, K. J., Ucker, D. S., and Kong, A.-N. T. (1998) Chemopreventive isothiocyanates induce apoptosis and Caspase-3-like protease activity. Cancer Res. 58, 402–408.
22. Sekharam, M., Trotti, A., Cunnick, J. M., and Wu, J. (1998) Suppression of fibroblast cell cycle progression in GI phase by N-acetylcysteine. Toxicol. and Appl. Pharm. 149, 210–216.
23. Chung, F.-L. Chemoprevention of lung carcinogenesis by aromatic isothiocyanates. In: Cancer Chemoprevention, Edition, (Wattenberg, L., Lipkin, M., Boone, C. W., Kelloff, G. J.) pp. 227–245, CRC Press Inc., 1992.
24. Chung, F.-L., Morse, M. A., Eklind, K. I. (1992) New potential chemopreventive agents for lung carcinogenesis of tobacco-specific nitrosamine. Cancer Res., 52, 2719s-2722s.
25. Wilkinson, J. T., Morse, M. A., Kresty, L. A., Stoner, G. D. (1995) Effect of alkyl chain length on inhibition of N-nitrosomethylbenzylamine-induced esophageal tumorigenesis and DNA methylation by isothiocyanates. Carcinogenesis 16, 1011–1015.
26. Jiao, D., Conaway, C. C., Wang, M.-H., Yang, C. S., Koehl, W., Chung, F.-L. (1996) Inhibition of N-nitrosodimethylamine demethylase in rat and human liver microsomes by isothiocyanates and their glutathione, L-cysteine, and N-acetyl-L-cysteine conjugates. Chem. Res. Toxicol., 92 932–938.
27. Sohn, O. S., Fiala, E. S., Puz, C., Hamilton, S. R., Williams, G. M. (1987) Enhancement of rat liver microsomal metabolism of azoxymethane to methylazoxymethanol by chronic ethanol administration: Similarity to the microsomal metabolism on N-nitrosodimethylamine. Cancer Res., 47,3123–3129.
28. Strobel, H. W., Fang, W.-F., and Oshinsky, R. J. (1980) Role of colonic cytochrome P-450 in large bowel carcinogenesis. Cancer, 45, 1060–1065.
29. Rao, C. V., Rivenson, A., Simi, B., Zang, E., Hamid, R., Kelloff, G. J., Steele, V., Reddy, B. S. (1995) Enhancement of experimental colon carcinogenesis by dietary 6-phenylhexyl isothiocyanate. Cancer Res., 55, 4311–4318.
30. Stoner, G. D., Siglin, J. C., Morse, M. A., Desai, D. H., Amin, S. G., Kresty, L. A., Toburen, A. L., Heffner, E. M., Francis, D. J. (1995) Enhancement of esophageal carcinogenesis in male F344 rats by dietary phenylhexyl isothiocyanate. Carcinogenesis, 16, 2473–2476.
31. Steinmetz, K. A., and Potter, J. D. (1991) Vegetables, fruits, and cancer, I. Epidemiology—Cancer Causes Control, 2, 325–357.
32. Chung, F.-L. Chemoprevention of lung carcinogenesis by aromatic isothiocyanates. In. Cancer Chemoprevention, Edition, (Wattenberg, L., Lipkin, M., Boone, C. W., Kelloff, G. J.) pp. 227–245, CRC Press Inc., 1992.
33. Hecht, S. S. Chemoprevention by isothiocyanates. (1995) J. Cell. Biochem., Suppl. 22, 195–209.
34. Sugie, S., Okamoto, K., Okumura, A., Tanaka, T., Mori, H. (1994) Inhibitory effects of benzyl thiocyanate and benzyl isothiocyanate on methylazoxymethanol acetate-induced intestinal carcinogenesis in rats. Carcinogenesis 15, 1555–1560.
35. Iatropoulos, M. J., Hard, G. C., Hecht, S. S. and Stoner, G. D. (1995). Three month toxicity study of phenethyl isothiocyante. Study No. R-1508, American Health Foundation, Valhalla, N.Y.
36. Levine, B. S. (1995) Thirteen week oral toxicity study of phenethyl isothiocyanate in dogs. NCI Contract No. NO1-CN25508-01. Toxicology Research Laboratory, University of Illinois at Chicago, Chicago, Ill.

We claim:

1. A method for inhibiting formation of aberrant crypts in the colon of a mammal comprising administering to the mammal a pharmacologically effective amount of an isothiocyanate selected from the group consisting of sulforaphane, phenethyl isothiocyanate and N-acetylcysteine conjugates thereof.

2. A method according to claim 1, wherein the isothiocyanate is sulforaphane.

3. A method according to claim 2, wherein the sulforaphane is administered to the mammal as a purified compound.

4. A method according to claim 1, wherein the isothiocyanate is phenethyl isothiocyanate.

5. A method according to claim 4, wherein the phenethyl isothiocyanate is administered to the mammal as a purified compound.

6. A method according to claim 1, wherein the isothiocyanate is administered to the mammal as a dietary supplement.

7. A method according to claim 1, wherein the mammal is a human.

8. A method according to claim 7, wherein the isothiocyanate is administered to the human in a dosage of between about 0.5 to 12 mg/kg body weight per day.

9. A method according to claim 1, wherein the isothiocyanate is the N-acetylcysteine conjugate of phenethyl isothiocyanate and is administered to the mammal after formation of aberrant crypts has initiated in the colon of the mammal.

10. A method according to claim 1, wherein the isothiocyanate is the N-acetylcysteine conjugate of sulforaphane.

11. A method according to claim 1, wherein the isothiocyanate is sulforaphane, phenethyl isothiocyanate or the N-acetylcysteine conjugate of sulforaphane and is administered to the mammal before initiation of aberrant crypt formation in the colon of the mammal.

12. A method according to claim 1, wherein the isothiocyanate is sulforaphane, phenethyl isothiocyanate or the N-acetylcysteine conjugate of sulforaphane and is administered to the mammal after formation of aberrant crypts has initiated in the colon of the mammal.

* * * * *